United States Patent
Esteron

(10) Patent No.: US 9,962,480 B2
(45) Date of Patent: May 8, 2018

(54) SYSTEM AND METHOD FOR OBTAINING A CELLULAR SAMPLE ENRICHED WITH DEFINED CELLS SUCH AS PLATELET RICH PLASMA (PRP)

(71) Applicant: ESTAR TECHNOLOGIES LTD, Holon (IL)

(72) Inventor: Aaron Esteron, Holon (IL)

(73) Assignee: ESTAR TECHNOLOGIES LTD, Holon (IL)

(*) Notice: Subject to any disclaimer, the term of this patent is extended or adjusted under 35 U.S.C. 154(b) by 433 days.

(21) Appl. No.: 14/373,978

(22) PCT Filed: Jan. 23, 2013

(86) PCT No.: PCT/IL2013/050061
§ 371 (c)(1),
(2) Date: Jul. 23, 2014

(87) PCT Pub. No.: WO2013/111130
PCT Pub. Date: Aug. 1, 2013

(65) Prior Publication Data
US 2014/0360944 A1 Dec. 11, 2014

Related U.S. Application Data

(60) Provisional application No. 61/589,401, filed on Jan. 23, 2012.

(51) Int. Cl.
*A61M 1/36* (2006.01)
*A61K 35/14* (2015.01)
(Continued)

(52) U.S. Cl.
CPC ........... *A61M 1/3672* (2013.01); *A61K 35/14* (2013.01); *A61K 35/16* (2013.01); *A61M 1/3693* (2013.01);
(Continued)

(58) Field of Classification Search
CPC ........... B04B 5/02; B04B 5/04; B04B 5/0407; B04B 5/0414; B04B 7/16; B04B 7/18;
(Continued)

(56) References Cited

U.S. PATENT DOCUMENTS 4,101,422 A 7/1978 Lamont et al.
4,148,764 A 4/1979 Lamont et al.
(Continued)

FOREIGN PATENT DOCUMENTS

EP 2 073 862 8/2016
WO 9617871 A1 6/1996
(Continued)

OTHER PUBLICATIONS

Eppley et al., Platelet Quantification and Grown Factor Analysis from Platelet-Rich Plasma: Implications of Wound Healing, Plastic and Reconstructive Surgery Journal of the American Society of Plastic Surgeons, Nov. 2004, pp. 1502-1508, vol. 114—Issue 6, Lippincott Williams & Wilkins.
(Continued)

*Primary Examiner* — Joseph Drodge
(74) *Attorney, Agent, or Firm* — Pearl Cohen Zedek Latzer Baratz LLP

(57) ABSTRACT

The invention relates to a system and method for obtaining a cellular fraction enriched with defined cells effective in promoting a defined cellular response from an in vivo cellular sample. The system is closable to the atmosphere, and includes a cell suspension collection tube containing gel and anticoagulant, adapted such that, when containing cell suspension and centrifuged after treatment the collection tube yields separation fractions, a first fraction comprising cellular fluid, a second fraction comprising gel layer, a third fraction comprising enriched cellular portion on top of the gel layer and a fourth fraction comprising a cell poor portion. The cell poor portion may be extracted and discarded prior to extracting the enriched cellular portion.

16 Claims, 3 Drawing Sheets

(51) Int. Cl.

| | |
|---|---|
| *A61K 35/16* | (2015.01) |
| *B01D 21/26* | (2006.01) |
| *B01D 21/30* | (2006.01) |
| *B01D 17/02* | (2006.01) |
| *B04B 5/04* | (2006.01) |
| *B04B 11/06* | (2006.01) |
| *B01L 3/00* | (2006.01) |
| *C12M 1/26* | (2006.01) |
| *A61M 1/02* | (2006.01) |

(52) U.S. Cl.
CPC ....... *B01D 17/0217* (2013.01); *B01D 21/262* (2013.01); *B01D 21/307* (2013.01); *B01L 3/50* (2013.01); *B04B 5/0414* (2013.01); *B04B 11/06* (2013.01); *C12M 1/264* (2013.01); *A61M 1/0272* (2013.01); *A61M 2202/0437* (2013.01); *A61M 2202/0462* (2013.01); *B01D 2221/10* (2013.01)

(58) Field of Classification Search
CPC ............ B04B 11/00; B04B 2005/0442; B04B 2005/0478; B01L 3/5021; B01L 2400/0409; B01L 2300/04; B01L 2300/046; B01L 2300/0681; B01L 3/50; B01L 3/56; B01L 3/565; B01D 21/26; B01D 21/262; B01D 21/307; B01D 17/0217; B01D 2221/10; A61M 1/02; A61M 1/0272; A61M 1/029; A61M 1/36; A61M 1/3672; A61M 1/3693; A61M 1/3696; A61M 2202/0437; A61M 2202/0462; A61K 35/16; A61K 35/14; A61K 35/19; G01N 2001/4088; G01N 33/49; G01N 33/491; G01N 33/5002; G01N 33/5073; C12M 1/26; C12M 1/264; C12M 33/04; C12M 33/06; C12M 33/10; C12M 33/14; C12M 47/12; C12M 1/12; C12M 1/265; C12N 5/0647; C12N 5/0662; C12N 5/0665
USPC ......... 210/360.1, 512.1, 781, 782, 787, 789; 422/72, 513, 521, 533, 534, 548, 549, 422/550; 436/45, 177; 424/93.7, 93.72; 435/287.1, 287.3, 287.9, 288.2, 298.2, 435/308.1, 366, 372
See application file for complete search history.

(56) References Cited

U.S. PATENT DOCUMENTS

| | | | |
|---|---|---|---|
| 4,190,535 A | 2/1980 | Luderer et al. | |
| 4,350,593 A | 9/1982 | Kessler | |
| 4,426,290 A * | 1/1984 | Ichikawa | B01D 43/00 210/516 |
| 4,828,720 A * | 5/1989 | Kuroda | B01D 43/00 210/516 |
| 4,946,601 A | 8/1990 | Fiehler | |
| 5,053,134 A | 10/1991 | Luderer et al. | |
| 5,236,604 A | 8/1993 | Fiehler | |
| 5,462,752 A | 10/1995 | Chao et al. | |
| 5,474,770 A | 12/1995 | Broly et al. | |
| 5,494,590 A | 2/1996 | Smith et al. | |
| 5,510,102 A | 4/1996 | Cochrum | |
| 5,510,237 A | 4/1996 | Isogawa et al. | |
| 5,525,612 A | 6/1996 | Gerster | |
| 5,533,518 A | 7/1996 | Vogler | |
| 5,585,007 A | 12/1996 | Antanavich et al. | |
| 5,663,051 A * | 9/1997 | Vlasselaer | B01L 3/5021 210/781 |
| 5,667,963 A | 9/1997 | Smith et al. | |
| 5,733,545 A | 3/1998 | Hood, III | |
| 5,906,744 A | 5/1999 | Carroll et al. | |
| 5,977,056 A | 11/1999 | Powell-Jones et al. | |
| 6,054,122 A | 4/2000 | MacPhee et al. | |
| 6,071,422 A | 6/2000 | Hlavinka et al. | |
| 6,117,425 A | 9/2000 | MacPhee et al. | |
| 6,197,325 B1 | 3/2001 | MacPhee et al. | |
| 6,368,298 B1 | 4/2002 | Beretta et al. | |
| 6,398,972 B1 | 6/2002 | Blasetti et al. | |
| 6,428,527 B1 | 8/2002 | Jones et al. | |
| 6,559,119 B1 | 5/2003 | Burgess et al. | |
| 6,979,307 B2 | 12/2005 | Beretta et al. | |
| 8,105,495 B2 * | 1/2012 | Dorian | A61M 1/3496 210/767 |
| 8,529,957 B2 | 9/2013 | Turzi et al. | |
| 8,734,373 B2 * | 5/2014 | Esteron | A61K 35/16 604/6.1 |
| 8,945,537 B2 | 2/2015 | Turzi | |
| 9,833,478 B2 | 12/2017 | Turzi et al. | |
| 2003/0233064 A1 | 12/2003 | Arm et al. | |
| 2004/0071786 A1 | 4/2004 | Grippi et al. | |
| 2004/0208786 A1 * | 10/2004 | Kevy | C07K 14/745 422/400 |
| 2004/0251217 A1 | 12/2004 | Leach et al. | |
| 2005/0008629 A1 | 1/2005 | Arm | |
| 2005/0112541 A1 * | 5/2005 | Durack | C12N 5/0612 435/2 |
| 2005/0205498 A1 | 9/2005 | Sowemimo-Coker et al. | |
| 2006/0175242 A1 * | 8/2006 | Dorian | A61M 1/0281 210/321.68 |
| 2006/0278588 A1 * | 12/2006 | Woodell-May | B01L 3/502 210/787 |
| 2007/0178018 A1 * | 8/2007 | Virno | B01L 3/5021 422/400 |
| 2008/0014181 A1 * | 1/2008 | Ariff | A61K 35/12 424/93.7 |
| 2008/0081367 A1 | 4/2008 | Sowemimo-Coker et al. | |
| 2008/0199845 A1 | 8/2008 | Rosiello et al. | |
| 2009/0208464 A1 * | 8/2009 | Centeno | A61K 35/28 424/93.7 |
| 2010/0159022 A1 | 6/2010 | Pedrozo et al. | |
| 2012/0027860 A1 * | 2/2012 | Katz | A61K 9/0019 424/489 |
| 2012/0237490 A1 * | 9/2012 | Karli | G01N 33/491 424/93.72 |
| 2012/0252650 A1 * | 10/2012 | Nash | B04B 1/02 494/36 |
| 2013/0244856 A1 * | 9/2013 | Nash | B01D 21/262 494/4 |
| 2015/0090650 A1 | 4/2015 | Grippi et al. | |
| 2015/0101995 A1 * | 4/2015 | Kim | A61M 1/3496 210/787 |

FOREIGN PATENT DOCUMENTS

| | | |
|---|---|---|
| WO | WO 98/56247 | 12/1998 |
| WO | WO 2004/084825 | 10/2004 |
| WO | 2005065269 A2 | 7/2005 |
| WO | WO 2008/023026 | 2/2008 |
| WO | 2010122548 A2 | 10/2010 |
| WO | 2011100458 A2 | 8/2011 |
| WO | 2011116221 A1 | 9/2011 |
| WO | WO2013061309 | 5/2013 |

OTHER PUBLICATIONS

Eppley et al., Platelet-Rich Plasma: A Review of Biology and Applications in Plastic Surgery, Plastic & Reconstructive Surgery Journal of the American Society of Plastic Surgeons, Nov. 2006, pp. 147e-159e, vol. 118—Issue 6, Lippincott Williams & Wilkins.

Kajikawa et al., Platelet-rich plasma enhances the initial mobilization of circulation-derived cells for tendon healing, Journal of Cellular Physiology, Jan. 2008, pp. 837-845, vol. 215—Issue 3, Wiley-Liss, Inc.

Otto, Jacques, Platelet Rich Plasma—Vampire Facelift, http://www.theottoclinic.ie/skin_rejuventation.htm.

(56) References Cited

OTHER PUBLICATIONS

International Search Report dated May 30, 2013 in corresponding International Application No. PCT/IL2013/050061.
Annunziata et al., "In vitro cell-type specific biological response of human periodontally related cells to platelet-rich plasma", J Periodont Res 2005; 40: 489 495.
Appel et al., "Comparison of three different preparations of platelet concentrates for growth factor enrichment", Clin. Oral Impl. Res, 13, 2002; 522-528.
Sadati et al., "Platelet Rich Plasma (PRP) Utilized to Promote Greater Graft Volume Retention in Autologous Fat Grafting", The American Journal of Cosmetic Surgery, vol. 23, No. 4, 2006, 203.
BD Vacutainer™ CPT™ Product Insert (2003).
BD Vacutainer® Tube Guide (2006).
Magalon et al., "DEPA classification: a proposal for standardising PRP use and a retrospective application of available devices", BMJ Open Sport Exerc Med, 2016; 2, pp. 1-5.
Castillo et al., "Comparison of Growth Factor and Platelet Concentration From Commercial Platelet-Rich Plasma Separation Systems", The American Journal of Sports Medicine, Nov. 4, 2010, pp. 1-6.
Celotti et al., "Effect of platelet-rich plasma on migration and proliferation of SaOS-2 osteoblasts: role of platelet-derived growth factor and transforming growth factor-$\beta$", Wound Rep Reg, (2006), 14, 195-202.
Weibrich et al., "Curasan PRP kit vs. PCCS PRP system Collection efficiency and platelet counts of two different methods for the preparation of platelet-rich plasma", Clin. Oral Impl. Res, 13, 2002; pp. 437-443.
Arkin et al., "Tubes and Additives for Venous Blood Specimen Collection; Approved Standard—Fifth Edition", NCCLS, H1-A5, vol. 23, No. 33, Dec. 2003, pp. 1-31.
Currie et al., "The Use of Fibrin Glue in Skin Grafts and Tissue-Engineered Skin Replacements: A Review", Plastic and Reconstructive Surgery, vol. 108, No. 6, Nov. 2001, pp. 1713-1726.
Doucet el al., "Platelet Lysates Promote Mesenchymal Stem Cell Expansion: A Safety Substitute for Animal Serum in Cell-Based Therapy Applications", J. Cell. Physiol. 205: 228-236,2005.
Eppley et al., "Platelet Quantification and Growth Factor Analysis from Platelet-Rich Plasma: Implications for Wound Healing", PRS vol. 114(6), Nov. 2004, pp. 1502-1508.
Everts et al., "Platelet rich plasma and platelet gel. A Review", J Extra Corpor Techn. 2006; 38:174-187.
Ferreira et al., "Platelet-rich plasma influence on human osteoblasts growth", Clin. Oral Impl. Res. 16, 2005; 456-460.
Fulton, "Breast Contouring with "Gelled" Autologous Fat: A 10-Year Update", International Journal of Cosmetic Surgery and Aesthetic Dermatology, vol. 5, No. 2, 2003, pp. 155-163.
Gadol et al., "A New Method for Separating Mononuclear Cells From Whole Blood", Diagnostic Immunology 3:145-154 (1985).
Graziani et al., "In vitro effects of different concentration of PRP on primary bone and gingival cell lines. Preliminary results.", Minerva Stomatal. Jan.-Feb. 2005;54(1-2):15-22.
Graziani et al., "The in vitro effect of different PRP concentrations on osteoblasts and fibroblasts", Clin. Oral. Impl. Res. 17, 2006; 212-219.
Hanson et al., "Interruption of acute platelet-dependent thrombosis by the synthetic antithrombin D-phenylalanyl-L-prolyl-L-arginyl chloromethyl ketone", Proc. Nati. Acad. Sci. USA, vol. 85, pp. 3184-3188, May 1988.
Haynesworth et al., "Mitogenic Stimulation of Human Mesenchymal Stem Cells by Platelet Releasale Suggests a Mechanism for Enhancement of Bone Repair by Platelet Concentrate, 48th Annual Meeting of the Orthopaedic Research Society, Poster No. 0462.
Hooiveld et al., "Haemoglobin-derived iron-dependent hydroxyl radical formation in blood-induced joint damage: an in vitro study", Rheumatology 2003;42:784-790.
Kaux et al., "Comparison of the platelet concentrations obtained in platelet-rich plasma (PRP) between the GPS™ II and GPS™ III systems", Pathologie Biologie (2010), pp. 1-4.
Lin et al., "Controlled release of PRP-derived growth factors promotes osteogenic differentiation of human mesenchymal stem cells", Conf Proc IEEE Eng Med Biol Soc. 2006;1:4358-61.
Leitner et al., "Platelet content and growth factor release in platelet-rich plasma: a comparison of four different systems", Vox Sanguinis (2006) 91, 135-139.
Liu et al., "Fibroblast proliferation due to exposure to a platelet concentrate in vitro is pH dependent", Wound Repair and Regeneration, vol. 10, No. 5, Sep.-Oct. 2002, pp. 336-340.
Liu et al., "Corneal Epitheliotrophic Capacity of Three Different Blood-Derived Preparations", IOVS, Jun. 2006, vol. 47, No. 6, pp. 2438-2444.
Marx, "Platelet-Rich Plasma: Evidence to Support Its Use", J Oral Maxillofac Surg, 62:489-496, 2004.
Marx et al., "Platelet-rich plasma: Growth factor enhancement for bone grafts", Oral Surgery Oral Medicine Oral Pathology, vol. 85, No. 6, Jun. 1998, pp. 638-646.
Sekisui Chemical Company, Material Safety Data Sheet, Serum Separating Gel, Feb. 21, 2003.
Centre Hospitalier Universitaire Vaudois, Effect of Platelet Rich Plasma and Keratinocyte Suspensions on Wound Healing, ClinicalTrails.gov Identifier: NCT00856934, Feb. 5, 2009 (available at www.clinicaltrials.gov).
Okuda et al., "Platelet-Rich Plasma Contains High Levels of Platelet-Derived Growth Factor and Transforming Growth Factor-$\beta$ and Modulates the Proliferation of Periodontally Related Cells in Vitro", J Periodontol, vol. 74, No. 6, Jun. 2003, pp. 849-857.
Oliva et al., "Ex vivo expansion of bone marrow stromal cells by platelet-rich plasma: a promising strategy in maxillo-facial surgery", Int J Immunopathol Pharmacol. Jul.-Sep. 2005;18(3 Suppl):47-53.
Perttila et al., "Plasma fibronectin concentrations in blood products", Intensive Care Med (1990) 16:41-43.
Shenkman et al., "Differential response of platelets to chemokines: RANTES non-competitively inhibits stimulatory effect of SDF-1$\alpha$", Journal of Thrombosis and Haemostasis, 2004; 2: 154-160.
Powell et al., "Recovery From Deep-Plane Rhytidectomy Following Unilateral Wound Treatment with Autologous Platelet Gel", Arch Facial Plast Surg, vol. 3, Oct.-Dec. 2001, pp. 245-250.
Raffoul et al., "Impact of platelets concentrate and keratinocyte suspension on wound healing—a prospective randomized trial", The International journal of artificial organs, Jul. 2008.
Regen Lab Brochure, "RegenPRP-KIT", available at wwwregenkit.com as of Sep. 26, 2004, pp. 1-18.
Regen Lab Presentation, "Innovation in Biological Tissue Regeneration", 2005, pp. 1-54.
Slichter et al., "Platelet Transfusion Therapy", Platelets in Hematologic and Cardiovascular Disorders, A Clinical Handbook, Cambridge University Press, 2008, pp. 242-260.
Tsay et al., "Differential Growth Factor Retention by Platelet-Rich Plasma Composites", American Association of Oral and Maxillofacial Surgeons, J Oral Maxillofac Surg 63:521-528, 2005.
Weibrich et al., "Growth stimulation of human osteoblast-like cells by thrombocyte concentrates in vitro", Mund Kiefer Gesichtschir, 2002 May;6(3):168-74.
Weibrich et al., "Effect of platelet concentration in platelet-rich plasma on peri-implant bone regeneration", Bone 34 (2004) 665-671.
Woodell-May et al., "Producing Accurate Platelet Counts for Platelet Rich Plasma: Validation of a Hematology Analyzer and Preparation Techniques for Counting", Journal of Craniofacial Surgery, Jan. 24, 2005, pp. 1-10.
Kajikawa et al., "Platelet-rich plasma enhances the initial mobilization of circulation-derived cells for tendon healing", J. Cell Physiology, Jan. 2008.
Cascade Medical Enterprises LLC, Fibrinet Autologous Fibrin & Platelet System, Instructions for Use, Jun. 6, 2006.
European Office Action for corresponding application No. 13 741 283.9 dated Feb. 20, 2018.

\* cited by examiner

SYSTEM AND METHOD FOR OBTAINING A CELLULAR SAMPLE ENRICHED WITH DEFINED CELLS SUCH AS PLATELET RICH PLASMA (PRP)

CROSS REFERENCE TO RELATED APPLICATIONS

This application is a U.S. national phase of PCT Application No. PCT/IL2013/050061, filed on Jan. 23, 2013, which claims priority from provisional application No. 61/589,401, filed on Jan. 23, 2012.

FIELD OF THE INVENTION

Various embodiments of the invention relate to systems and methods for preparing a cellular fraction enriched with defined cells reported to be effective in promoting a defined cellular response from an in vivo cellular sample and more particularly systems and methods for preparing a platelet-rich plasma (PRP), enriched mesenchymal stem cells (MSC) or enriched bone marrow stem cells (BMSC) sample.

BACKGROUND OF THE INVENTION

The bone tissue is composed of bone matrix and bone cells. Bone matrix comprises mainly type I collagen as well as other proteins, including osteocalcin and osteonectin. These and other proteins take part in matrix maturation, mineralization and may regulate the functional activity of bone cells, the latter being primarily osteoblasts and osteoclasts. Osteoblasts are bone-forming cells and osteoclasts are bone resorbing cells. The main function of the bone cells is to mediate bone remodeling mechanisms in order to maintain the integrity of the skeleton by removing old bone of high mineral density and high prevalence of fatigue microfractures through repetitive cycles of bone resorption and bone formation. During bone formation phase, the osteoblasts are recruited from stem cells population present in bone marrow.

There are two main populations of stem cells in the bone marrow: hematopoietic stem cells (HSC), which give rise to all blood cell lineages including erythrocytes, platelets, and white blood cells), and mesenchymal stem cells (MSC). The MSC are self-renewing, clonal and multipotent precursors of nonhematopoietic tissues, capable of differentiating into osteoblasts, chondrocytes, astrocytes, pneumocytes, hepatocytes, neurons, and cardiac myocytes.

Bone marrow-derived stem cells (BMSCs) contribute to tissue repair or regeneration of a broad spectrum of tissues including myocardium, cardiac valves, blood vessels, damaged bone, simple bone cysts, and fracture delayed union or non-union tendon, cartilage, 2 meniscus, and skin. Bone marrow aspiration can be obtained from any of the standard autograft locations, e.g., iliac crest, proximal/distal tibia, or calcaneus. Standard technique for BM aspiration is withdrawal of the later using a suitable needle, such as trocar or bone marrow biopsy needle and an anticoagulant-containing syringe.

PRP is a product of blood plasma that is rich in platelets. PRP may be used in a variety of therapeutic or cosmetic applications including enhancing wound healing in dental implants and sinus elevations, heart surgery, orthopedic surgery, and dermatology (chronic wound healing) [Barry L. et al, Plastic Reconstructive Surgery 114(6): pp. 1502-1508, 2004; Barry L. et al, Plastic Reconstructive Surgery 118(6): 147e-15, 2006; and Kajikawa Y. et al, J. Cell Physiol., 215(3): pp. 837-45, 2008; and Jacques Otto (published online: http://www.theottoclinic.ie/skin_rejuvenation.htm). PRP may also be utilized as a culture medium for cell expansion in the laboratory.

WO2005/065269 discloses several compositions comprising PRP and fibroblast cells for the treatment of skin, in particular, repeated administration of PRP in a dermatologically acceptable carrier to skin to e.g. reduce appearance of wrinkles.

Thus there is a long unmet need to provide methods and means to obtain PRP, MSC and BMSC, in a state ready for use in therapeutic or cosmetic applications or procedures.

SUMMARY OF INVENTION

It is an object of the present invention to disclose a system for obtaining a cellular fraction enriched with defined cells effective in promoting a defined cellular response from an in vivo cellular sample comprising:
(a) a collection tube for collecting a cell suspension (1), (b) an anticoagulant portion (4); (c) a portion of separation gel (3); (d) a first collection syringe for collecting a cell depleted fluid (10); (e) a second collection syringe for collecting the enriched cellular portion (11); and (f) at least one needle (10) for attaching to each syringe.

The system is closable to the atmosphere; further wherein the cell suspension collection tube contains the gel (3) and the anticoagulant (4); the tube is adapted such that, when containing cell suspension and centrifuged after treatment yields separation fractions, a first fraction comprising cellular fluid (6), a second fraction comprises gel layer (3), a third fraction comprises enriched cellular portion (7) on top of the gel layer and a fourth fraction comprises a cell poor portion (8).

It is another object of the present invention to provide the system as defined above, wherein the system is adapted such that the cell poor portion is discardable with the first collection syringe with the needle.

It is another object of the present invention to provide the system as defined above, wherein the second collection syringe with the needle are dimensionally configured for extraction of cells remaining after re-suspending of the enriched cellular portion.

It is another object of the present invention to provide the system as defined above, wherein the cell suspension is a peripheral blood sample or stem cell-containing cellular sample derived from tissue such as bone marrow or adipose stem cells.

It is one object of the present invention to provide a system for obtaining a low medium density fraction enriched with defined cells effective in promoting a defined cellular response from an in vivo cellular sample comprising:
(a) a collection tube for collecting a cell suspension (1); (b) an anticoagulant portion (4); (c) a portion of separation gel (3); (d) a first collection syringe for collecting a cell depleted fluid (10); (e) a second collection syringe for collecting the enriched cellular portion (11) and, (f) at least one needle for attaching to each syringe.

The system is closable to the atmosphere, further wherein the cell suspension collection tube contains the gel (3) and the anticoagulant (4); the tube is adapted such that, when containing cell suspension and centrifuged yields fractions of different densities, a first high density fraction (6), a second medium-high density fraction (3), a third medium-low density fraction (7) on top of the gel layer and a fourth fraction low density fraction (8), the third medium-low density fraction substantially containing enriched defined cells; the enriched defined cells selected from the group consisting of enriched bone marrow stem cells, enriched MSC, and platelet rich plasma (PRP).

It is one object of the present invention to provide a system for obtaining an enriched mesenchymal stem cell (MSC) portion comprising: (a) a collection tube for collecting cell suspension (1), (b) at least one stopper (2), (c) an anticoagulant portion (4), (d) a portion of separation gel (3), a first collection syringe for collecting poor cellular fluid (10), (d) a second collection syringe for collecting mesenchymal stem cells (MSC) (11), and (e) at least one needle (10) for attaching to each syringe.

The system is closable to the atmosphere; further wherein the collection tube comprising the gel (3) and the anticoagulant (4); the collection tube containing cell suspension is adapted such that, when containing the cell suspension (5) and centrifuged after treatment yields separation fractions, a first fraction comprises primarily red blood cells (RBCs), a second fraction comprises gel layer (3), a third fraction comprises cellular fraction containing MSC (7) on top of the gel layer and a fourth fraction comprises poor cellular fluid (8).

It is another object of the present invention to provide the system as defined above, wherein the system is adapted such that the poor cellular fluid is discardable with the first collection syringe.

It is another object of the present invention to provide the system as defined above, wherein the second collection syringe and the needle are dimensionally configured for extraction of the enriched MSC remaining after re-suspending of the MSC portion.

It is one object of the present invention to provide a system for obtaining an enriched bone marrow fraction comprising:
(a) a collection tube for collecting bone marrow, (b) at least one stopper; (c) an anticoagulant portion, (d) a portion of separation gel; (e) a first collection syringe for collecting poor cells fluid, (f) a second collection syringe for collecting enriched bone marrow cells and, (g) at least one needle for attaching to each syringe.

It is another object of the present invention to provide the system as defined above, wherein the system is closable to the atmosphere; further wherein the collection tube for collecting bone marrow contains the gel and the anticoagulant; the tube containing the bone marrow is adapted such that when centrifuged after treatment yields separation fractions, a first fraction comprises primarily red blood cells (RBCs) sediment, a second fraction comprises gel layer, a third fraction comprises enriched bone marrow cells on top of the gel layer and a fourth fraction comprises poor cellular fluid.

It is another object of the present invention to provide the system as defined above, wherein the poor cellular fluid is discarded using the first collection syringe.

It is another object of the present invention to provide the system as defined above, wherein the second collection syringe with the needle are dimensionally configured for extraction of the enriched bone marrow cells after re-suspending of the remaining bone marrow cells portion.

It is another object of the present invention to provide the system as defined above, further comprising means for treating cell aspirate before the latter is applied into the collection tube.

It is one object of the present invention to provide a system for obtaining platelet rich plasma (PRP) comprising: (a) a collection tube for collecting blood (1), (b) at least one stopper (2), (c) an anticoagulant portion (4), (d) a portion of separation gel (3), (e) a first collection syringe for collecting platelets poor plasma (PPP) (10), (f) a collection syringe for collecting platelets rich plasma (PRP) (11), and (g) at least one needle for attaching to each the syringe. The system is closable to the atmosphere; further wherein the collection tube comprising the gel (3) and the anticoagulant (4); the collection tube is adapted such that when containing the whole blood (5) and centrifuged after treatment yields separation fractions, a first fraction comprises red blood cells (RBCs) sediment and granulocytes (6), a second fraction comprises gel layer (3), a third fraction comprises platelets (7) on top of the gel layer and a fourth fraction comprises platelets poor plasma (PPP) (8).

It is another object of the present invention to provide the system as defined above, wherein the PPP portion is discardable using a platelets poor plasma (PPP) collection syringe.

It is another object of the present invention to provide the system as defined above, wherein the collection syringe for collecting platelets rich plasma (PRP) with the needle are dimensionally configured for extraction of the remaining PRP after re-suspending of the PRP portion.

It is one object of the present invention to provide a system for obtaining platelet rich plasma (PRP) comprising: (a) a collection tube for collecting blood (1), (b) at least one stopper (2), (c) an anticoagulant (4), (d) a separation gel (3), (e) a collection syringe for collecting platelets poor plasma (PPP) (10), (f) a collection syringe for collecting platelet rich plasma (PRP) portion (11); and (g) at least one needle for attaching to each syringe, wherein the system is closable to the atmosphere; further wherein the collection tube is a vacuum tube and the separation gel and the anticoagulant is in the tube; further wherein the collection syringe for collecting platelets rich plasma (PRP) portion further comprises a filter unit of 3-50 μm for obtaining WBC-selective PRP.

It is another object of the present invention to provide the system as defined above, further comprises a filter unit of 3-50 μm.

It is another object of the present invention to provide the system as defined above, wherein the collection tube is selected from the group consisting of: a vacuum, tube, a non-vacuum tube, a plastic tube, a glass tube, a rigid tube, a non-rigid tube, a semi rigid tube and any combination thereof.

It is another object of the present invention to provide the system as defined above, wherein the vacuum tube is adapted such that, when containing the whole blood (5), and centrifuged after treatment, yields separation fractions comprising, a first fraction of RBCs sediment and granulocytes (6), a second fraction of the gel (3), a third fraction comprising platelets (7), and fourth fraction of PPP (8)

It is another object of the present invention to provide the system as defined above, wherein the collection syringe for collecting platelets poor plasma (PPP) is adapted for discarding PPP.

It is another object of the present invention to provide the system as defined above, wherein the platelets rich plasma (PRP) collection syringe is adapted for drawing the remaining PRP after re-suspending of the PRP portion.

It is another object of the present invention to provide the system as defined above, further comprising a stopcock adapted as a turning plug which controls the flow of fluid from the PPP collection syringe to the blood collection tube.

It is another object of the present invention to provide the system as defined above, further comprising a stopcock adapted as a turning plug which controls the flow of fluid from the PRP portion collection syringe to the blood collection tube.

It is another object of the present invention to provide the system as defined above, wherein the anticoagulant is selected from the group consisting of: buffer citrate, ACD, modified ACD (citric/citrate dextrose), heparinate salts, EDTA salts, iodo acetate salts, oxalate salts, fluoride salts as water solutions or lyophilized material or wet or dry spray on inner wall and so forth and any combination thereof.

It is another object of the present invention to provide the system as defined above, wherein the anticoagulant comprises any type of anticoagulant designed for preventing clotting of blood.

It is another object of the present invention to provide the system as defined above, wherein the separation gel is at density of 1.04-1.09 g/cm$^3$.

It is another object of the present invention to provide the system as defined above, wherein the centrifugation is performed for about 10-30 min.

It is another object of the present invention to provide the system as defined above, wherein the PPP is discardable up to 90% of plasma from the blood collection tube.

It is another object of the present invention to provide the system as defined above, wherein the PPP is discardable at least 50% of plasma from the blood collection tube.

It is another object of the present invention to provide the system as defined above, wherein the PPP is discarded about 90% of plasma from the blood collection tube.

It is another object of the present invention to provide the system as defined above, wherein the collection syringe for collecting platelets rich plasma (PRP) contains additives selected from the group consisting of: Hyaluronic acid (HA), collagen, allograft bone, autograft bone, bone substitutes, autologous adults stem cells, $CaCl_2$, thrombin, collagen and any combination thereof.

It is another object of the present invention to provide the system as defined above, wherein the collection syringe for collecting platelets rich plasma (PRP) is adapted for a mixture of the obtained platelet rich plasma (PRP) with an activating agent selected from the group consisting of Thrombin $CaCl_2$, collagen and ADP.

It is one object of the present invention to provide a method for producing platelet rich plasma (PRP), the method comprising steps of:
(a) obtaining a closable system for preparing platelet rich plasma (PRP) comprising:
(i) a collection tube for collecting blood (1), (ii) at least one stopper (2);
(iii) an anticoagulant (4), (iv) a separation gel (3), (v) a collection syringe for collecting platelets poor plasma (PPP) (10), (vi) a collection syringe for collecting platelets rich plasma (PRP) portion (11), and (vi) at least one needle for attaching to each syringe, and
(b) placing the anticoagulant portion and the portion of separation gel in the tube:
(c) filling the collection tube for collecting blood with whole blood sample,
(d) separating by centrifugation there by obtaining separation fractions comprising, a first fraction of RBCs sediment and granulocytes, a second fraction of the gel, a third fraction of platelets, and fourth fraction of PPP solution, (e) discarding a portion of PPP with the first collection syringe combined with the needle:
(f) re-suspending of the platelets with other separated blood components, (g) extracting the remaining PRP and portion of WBCs solution with the PRP collection syringe; such that a WBC-selective PRP is obtained.

It is one object of the present invention to provide a method for producing of enriched stem cells sample, the method comprising steps of:
(a) obtaining a closable system for obtaining a cellular fraction enriched with defined cells effective in promoting a defined cellular response from an in vivo cellular sample comprising:
(i) a collection tube for collecting a cell suspension (1), (ii) at least one stopper (2); (iii) an anticoagulant portion (4), (iv) a portion of separation gel (3), (v) a first collection syringe for collecting a cellular sample, (vi) a second collection syringe for collecting the enriched cellular portion; and, (vii) at least one needle (10) for attaching to each syringe, and
(b) placing the anticoagulant portion and the portion of separation gel in the tube,
(c) filling cell suspension with cell culture sample, (d) separating by centrifugation, thereby obtaining separation fractions comprising, a first fraction of cell suspension, a second fraction of the gel, a third fraction of enriched cellular portion, and fourth fraction of poor cellular fluid, (e) discarding a portion of poor cellular fluid with the first collection syringe combined with the needle, (f) re-suspending of the cellular fluid with other separated cell components, and (g) extracting the remaining enriched cellular portion with the enriched cellular portion collection syringe such that an enriched selective stem cells fraction is obtained.

It is another object of the present invention to provide the method as defined above, wherein the third fraction is re-suspended to obtain PRP.

It is another object of the present invention to provide the method as defined above, wherein the step of extracting the remaining PRP and portion of WBCs solution is with PRP collection syringe attached to a filter unit.

It is another object of the present invention to provide the method as defined above, wherein the step of extracting the remaining enriched cellular portion with the enriched cellular portion collection syringe is with a filter unit.

It is another object of the present invention to provide the method as defined above, including discarding up to 90% of PPP from the blood collection tube.

It is another object of the present invention to provide the method as defined above, including discarding about 90% of PPP from the blood collection tube.

It is another object of the present invention to provide the method as defined above, wherein the anticoagulant comprises any type of anticoagulant designed for preventing clotting of blood.

It is another object of the present invention to provide the method as defined above, wherein the enriched cellular portion collection syringe contains additives selected from the group consisting of: Hyaluronic acid (HA), collagen, allograft bone, auto graft bone, bone substitutes, autologous adults stem cells, $CaCl_2$, thrombin, collagen and any combination thereof.

It is another object of the present invention to provide the method as defined above, wherein the enriched cellular fraction is optimally transferred using the second collection syringe to a vessel containing additives selected from the group consisting of: Hyaluronic acid (HA), collagen, allograft bone, auto graft bone, bone substitutes, autologous adults stem cells, $CaCl_2$, thrombin, collagen and any combination thereof.

It is another object of the present invention to provide the method as defined above, wherein the PRP collection syringe comprises at least two split barrels, whilst one of the barrels contains activators or/and additives and another barrel serves for PRP collection.

It is another object of the present invention to provide the method as defined above, further comprising the step of mixing the concentrated PRP or stem cell portion with hemostat or biodegradable scaffolds It is another object of the present invention to provide the method as defined above, further comprising the step of mixing the obtained platelet rich plasma (PRP) with an activating agent selected from the group consisting of Thrombin, $CaCl_2$, collagen and ADP.

It is another object of the present invention to provide the method as defined above, wherein the filter unit is of 3-50 μm.

It is another object of the present invention to provide the method as defined above, wherein the tube is selected from the group consisting of: a vacuum tube, a non-vacuum tube, a plastic tube, a glass tube, a rigid tube, a non rigid tube, a semi rigid tube and any combination thereof.

It is another object of the present invention to provide the method as defined above, wherein the separation gel is at density of 1.04-1.09 g/cm$^3$.

It is another object of the present invention to provide the method as defined above, including discarding up to 90% of PPP from the blood collection vacuum tube.

It is another object of the present invention to provide the method as defined above, including discarding about 90% of PPP from the blood collection vacuum tube.

It is another object of the present invention to provide the method as defined above, wherein the anticoagulant is selected from the group consisting of: buffer citrate, ACD, modified ACD (citric/citrate dextrose), heparinate salts, EDTA salts, iodo acetate salts, oxalate salts, fluoride salts as water solutions or lyophilized material or wet or dry spray on inner wall and so forth and any combination thereof.

It is another object of the present invention to provide the method as defined above, wherein the anticoagulant comprises any type of anticoagulant designed for preventing clotting of blood.

It is another object of the present invention to provide the method as defined above, wherein the platelets rich plasma (PRP) collection syringe includes additives selected from the group consisting of: Hyaluronic acid (HA), collagen, allograft, auto graft bone, bone substitutes, autologous adults stem cells, $CaCl_2$, thrombin, collagen and any combination thereof.

It is another object of the present invention to provide the method as defined above, further comprising the step of mixing the obtained platelet rich plasma (PRP) with an activating agent selected from the group consisting of Thrombin, $CaCl_2$, collagen and ADP.

BRIEF DESCRIPTION OF THE INVENTION

In order to understand the invention and to see how it may be implemented in practice, a few preferred embodiments will now be described, by way of non-limiting example only, with reference to be accompanying drawings, in which.

DETAILED DESCRIPTION OF EMBODIMENTS

Figure 1:
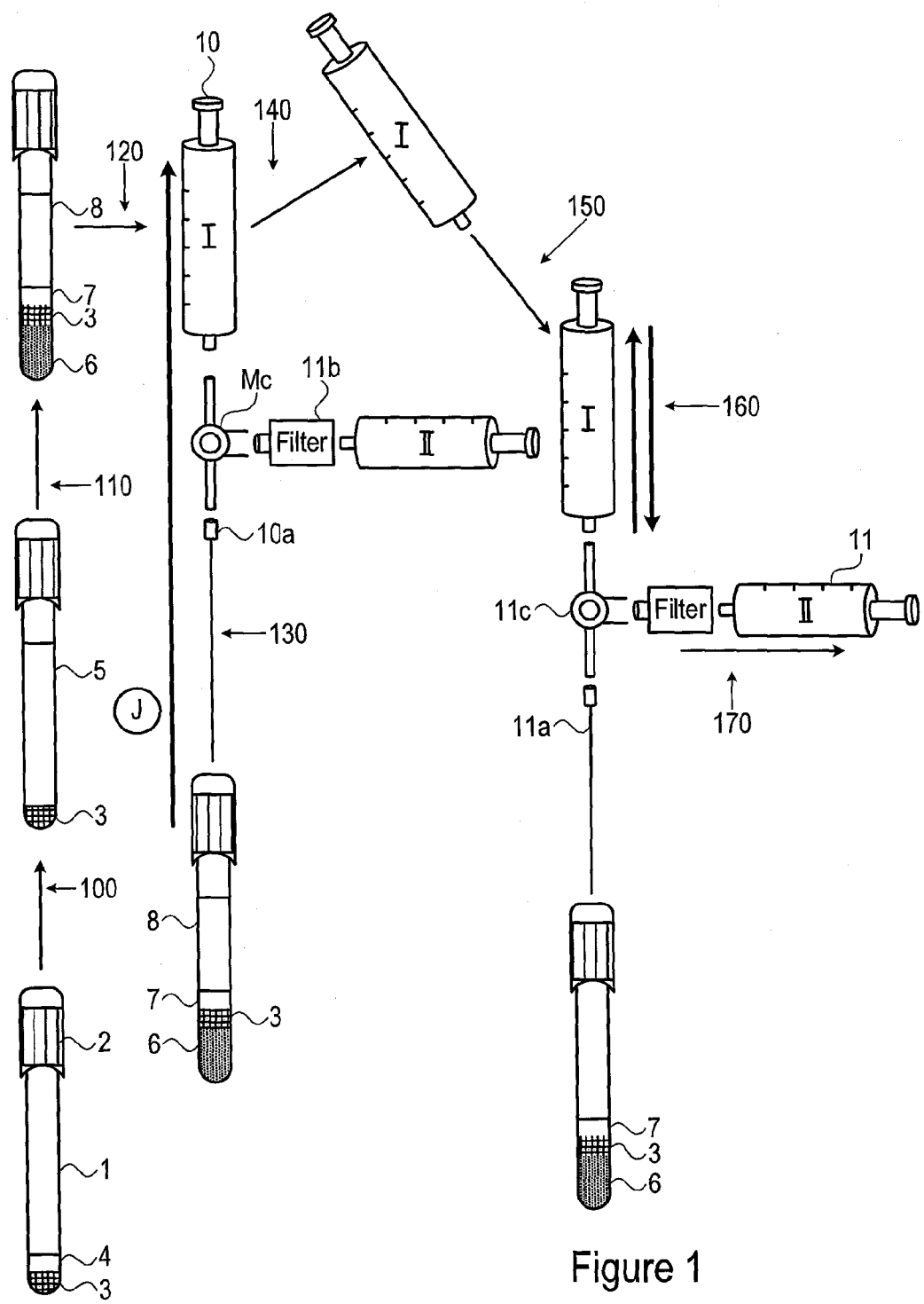
FIG. 1 shows a closed system for derivation of WBC-selective PRP, in accordance with a preferred embodiment of the present invention.

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide methods and systems for producing high levels of platelet rich plasma (PRP).

The term "PRP" or "platelet rich plasma" as used herein should be understood to mean a blood-derived product which comprises platelets concentrated in a small volume of plasma.

The term "WBC-selective PRP" as used herein should be understood to encompass PRP having reduced number of white blood cells or a selective population of WBCs. The term "WBC-selective PRP" typically refers to a PRP that comprises WBCs at a concentration which is less than 50%, at times less than 40%, 30%, 20%, 10%, 5%, 4%, 3%, 2% or even less than 1% than that in the blood. The term "WBC-selective PRP" may also refer to PRP devoid of a certain population of WBCs, typically such that are filtered-out by a filter with a certain pore size.

The PRP obtained in accordance with the invention may be used for treating aging skin and wrinkled-skin cells, accelerating healing of bone cells, treating surgery wounds, diabetic wounds, ulcer wounds, and pressure wounds and is used as autologous biological cells formation and/or biological glue.

In particular, some exemplary embodiments of the invention enable the preparation of PRP in a practitioner's treatment settings. The preparation of a WBC-selective PRP according to the invention is relatively rapid, e.g. about 15, 30, 40, 50 or 60 minutes.

The term "Stem cell" as used herein should be understood to mean biological cells or vehicle found in all multicellular organisms. Accessible sources of autologous adult stem cells are Bone marrow, Adipose tissue (lipid cells), umbilical cord blood. and hematopoetic blood.

In accordance with the preferred embodiment of the present invention all the elements of the invention, such as tubes, syringes etc., are combined in a closed system. The closed system eliminates direct contact with the fluid path, while helping to reduce the danger of contamination and infection. It is known in the art that whole blood components collected in a non-sterile, or "open", system (i.e. one that is open to communication with the atmosphere) must, under governmental regulations, be transfused within twenty-four hours. However, when cell suspensions such as bone marrow, adipose stem cells or whole blood components are collected in a sterile, or "closed", system (i.e., one that is closed to communication with the atmosphere), the cell suspension or red blood cells can be stored up to forty-two days (depending upon the type of anticoagulant and storage medium used); the platelet concentrate can be stored up to five days (depending upon the type of storage container); and the platelet-poor plasma may be frozen and stored for even longer periods. The apparatus and methods that embody the features of the invention are particularly well suited for use in association with closed blood collection systems and conventional sterile connection techniques, thereby permitting separation to occur in a sterile, closed environment.

The present invention provides systems and methods for separating platelets from peripheral blood or from tissue derived cellular samples, such as bone marrow, umbilical cord blood, blood or adipose stem cells respectively.

The present invention presents a system for obtaining a cellular fraction enriched with defined cells, which have been reported to be effective in promoting a defined cellular response from an in vivo cellular sample comprising: (a) a collection tube for collecting a cell suspension, (b) at least one stopper, (c) an anticoagulant portion, (d) a portion of separation gel, (e) a first collection syringe for collecting a plasma or cellular sample, (f) a second collection syringe for collecting the enriched cellular portion and, (g) at least one needle (10) for attaching to at least one of the syringes.

The system is closable to the atmosphere. The cell suspension collection tube contains the gel and the anticoagulant and blood or cell suspension sample or cell culture. The tube containing cell suspension is adapted such that, when centrifuged after treatment yields separation fractions, a first fraction comprising cellular fluid, a second fraction comprises gel layer, a third fraction comprises enriched cellular portion on top of the gel layer and a fourth fraction comprises the cell poor portion.

The system is further adapted such that the enriched cellular portion is harvested with a collection syringe with a needle. for collecting cellular samples.

Furthermore, the collecting of an enriched cellular portion with the needle is dimensionally configured for extraction of cells remaining after re-suspending of the enriched cellular portion. Isolation of stem cells may be performed whether from somatic tissues, or whole blood. Protocols may further be used to be adjusted based on the stem cell source or species.

The present invention further provides a method of direct aspiration into a vacuum bone marrow collection tube using a suitable needle that penetrates the bone. BM aspirate should be mixed with anticoagulant and processed for mononuclear cells separation.

The present invention further provides a system which includes a centrifugation to obtain PRP or BM-/adipose/umbilical cord blood derived mesenchymal stem cells (MSC) or Hematopoietic stem cells. The Hematopoietic and MSC are nucleated cells, whilst platelets are anucleated cytoplasmic fragments of megakaryocyes. Therefore, different separation gel having different density is applied for PRP and MSC separation. The concentrated solution of BMSC comprises different progenitor cells such as mesenchymal stem cells (MSC), hematopoietic stem cells (HSCs), endothelial progenitor stem cells (EPCs). These cells as well as PRP, promote cellular responses and tissue repair by secreting trophic, paracrine, and growth factors which play a key role in the wound-healing process by initiating and maintaining cell proliferation, angiogenesis, matrix deposition and the like.

In another embodiment of the present invention, Hematopoietic and MSCs have the ability to differentiate, and they help to establish new vascular and musculoskeletal tissues. Furthermore, concentrated hematopoietic stem cells or mesenchymal stem cells may be used to treat certain hematological malignancies.

In another embodiment of the present invention, a possible implementation of PRP or MSC treatment for bone-healing purposes, is the bone graft (i.e., autograft, allograft, or synthetic) which may be soaked in PRP or mixed/infused with MSC. Furthermore, PRP and/or stem cell concentrate may be mixed with hemostat or biodegradable scaffolds for internal or external (for example wounds, dentistry) use. Human adipose tissue obtained by liposuction, can be processed to obtain a population of cells such as processed lipoaspirate (PLA). This tissue, in addition to adipogenic, endothelial and vascular progenitor cells, also contains multipotent cell types, termed adipose stem cells (ADSCs), which have the ability to undergo self-renewal and multilineage differentiation to bone, cartilage and muscle, as well as fat, similarly to their bone marrow-derived counterparts. The use of autologous ASCs as cellular regeneration therapy is both safe and efficacious in preclinical and clinical studies of injury and disease.

Without wishing to be bound by theory, Platelet-rich plasma can enhance the proliferation of human ADSCs. Furthermore, peripheral blood may be processed to obtain concentrated stem cell portion. Peripheral blood contains circulating hematopoietic stem cells and their concentration in the blood, can be markedly elevated by administration of known substances, such as granulocyte colony-stimulating factor (G-CSF), which is used in leukopheresis techniques to increase significantly the number of stem cell progenitors in the circulation by inducing. This is being referred to as mobilized peripheral blood.

In another embodiment of the present invention, umbilical cord blood is a source of hematopoietic stem (HSC) and progenitor cells for the treatment of a variety of malignant and non-malignant disorders. The system described herein can be used to obtain stem cell concentrate from cord blood for cryopreservation and treatment.

Reference is herein made to FIG. 1 which illustrates a closable system for obtaining platelet rich plasma (PRP) in whole blood sample.

A closable system for producing PRP comprises: (a) a blood collection tube 1, (b) at least one stopper 2, (c) an anticoagulant portion 4, (d) a portion of separation gel 3, (e) a platelets poor plasma (PPP) collection syringe 10 including sharp long needle 10a, and (f) a platelets rich plasma (PRP) collection syringe 11 including sharp long needle 11a.

In some embodiments, the test tube 1 is provided with a stopper, a cover or any closer 2, typically made of rubber.

In some embodiments, test tubes are made of glass or MPA (modified poly Amide) or modified PET (Poly Ethylene Terephthalate). In some embodiments, the test tube has a layered structure such that the interior wall of the test tube comprises polypropylene. Test tubes can further be provided with a special stopper. By way of a non-limiting example the cover is made of butyl rubber or its halo derivative formulations at hardness between 40-60 Shore A. The hardness assures stable vacuum for at least the shelf life of the test tube which can be between 18-24 months. The tube can be vacuum or non-vacuum. For non-vacuum tubes, blood is drawn by standard means, such as a needle and syringe and transferred into the tube through a security opening, which sustains closed system environment.

The test tubes used can be of various sizes which depend on the required quantity of whole blood/cellular fluid to be drawn from the treated subject. The test tubes have typically a size suitable for blood samples in the range of 4 ml to 100 ml.

The collection tube is selected from the group consisting of: vacuum, a non vacuum tube, a rigid tube, a non-rigid tube, a semi-rigid tube, plastic tube, glass tube, and any combination thereof.

In accordance with the preferred embodiment of the present invention, FIG. 1 shows the vacuum tube 1 consisting of a separation gel 3 layer at a density of 1.04-1.09 g/cm³ and an anticoagulant layer 4. The anticoagulant 4 is selected from the group consisting of: such as, but not limited to buffer citrate, ACD, modified ACD (citric/citrate dextrose), heparinate salts, EDTA salts, iodo acetate salts, oxalate salts, fluoride salts as water solutions or lyophilized material or wet or dry spray on inner wall and so forth, or any type of anticoagulant designed for preventing clotting of blood.

In some embodiments, test tubes contain a barrier-forming substance to assist in the centrifugation-based separation of blood into its components. Such barrier-forming substance may be of the kind known per se, for example gel polymers. Gel polymers may, for example, be based on polyacrylic, polyolefin or polyester with a specific gravity in the range of about 1.04 to 1.09 g/cm³.

In a first step of the procedure, whole blood sample 5 withdrawn from a subject is inserted into a blood collection tube which comprises the gel layer 3 and the anticoagulant layer 4. In order to perform a separation of whole blood 5 a centrifugation procedure 110 is performed on the basis of specific gravity at 300-2000 g for about 10 to about 30 minutes, resulting in four fractions. Following centrifugation 110, blood components, particularly red blood cells and most of the granulocytes 6, will remain beneath the gel barrier 3 and other components, including platelets, will remain above it. The first and heaviest fraction at the bottom of the tube comprises red blood cells (RBCs) and most of the granulocytes layer 6 as a sediment layer, the second fraction comprises the gel layer 3, the third fraction, on the top of the gel, comprises platelet rich plasma (PRP) as a thin layer 7, and the last (fourth) fraction comprises platelet poor plasma (PPP) solution 8 as a supernatant layer. The system remains closed in all of the steps of the procedure and the blood does not coagulate or become contaminated.

In yet another embodiment of the invention, while test tube may optionally include an anti-coagulant, in some procedures an anti-coagulant may a priori not be included. For example, if the blood sample is withdrawn and maintained in cold conditions, an anti-coagulant may not be needed. In addition, in some procedures, the anti-coagulant may be mixed with the whole blood which was withdrawn from a subject, prior to inserting the whole blood into the tube.

Through agitation/mixing, it can then mix with the anti-coagulant, optionally included within the test tube. Alternatively, the blood sample may be mixed with an anti-coagulant, prior to insertion into tube. The test tube is then subjected to centrifugation. Centrifugation is used to separate the red blood cells (RBCs) and most of the granulocytes from the plasma and the platelets.

Centrifugation may, for example, be at about 300-2000 g and for a time period of 10-30 minutes. Centrifugation results in platelet enrichment 2-10 times compared to their native concentration in whole blood.

In yet another embodiment of the invention, anticoagulant will be used, the blood collection tube containing separation gel layer and whole blood sample will be centrifuged, resulting in four fractions: the first and heaviest fraction at the bottom of the tube comprises red blood cells (RBCs) and most of the granulocytes layer 6 as a sediment layer, the second fraction comprises the gel layer 3 as a barrier between the RBCs fraction and a plasma fraction, the third fraction comprises PRP 7, on the top of the gel, and the last fraction comprises PPP solution 8. After centrifugation 110 a PPP collection syringe 10 with a sharp long needle 10a is inserted into the blood collection tube 120 and a portion of PPP 8 is removed 130 from the tube. The platelets are concentrated at the bottom end of the plasma fraction, typically forming a pellet. Typically, more than half of the plasma is PPP, therefore removal of more than half of the upper phase in the blood collection tube is required. By removal of part of the plasma to yield more enriched plasma and by subsequent agitation, a PRP fraction 7 is obtained.

In some embodiments of the invention the amount of PPP 8 which extracted from the blood collection tube 1 is up to 90% of PPP. In another embodiment of the invention, the amount of PPP 8 which extracted from the tube 1 is at least 90% of PPP. In yet another embodiment of the invention the amount of PPP which extracted from the tube 1 is about 90% of PPP.

Extraction of the PPP from the tube is performed using a collection syringe with optional 1-3 way stopcock 11c attached to a long sharp needle 11a.

In another embodiment of the invention, the PRP collection syringe 11 may also include a filter unit 11b having an effective pore size of about 3-50 μm such to permit passage of platelets and not permit passage of white blood cells (WBCs).

Re-suspending of the platelets with optional separated blood components 160 such as WBCs and growth factors is performed via repeated inversion of the tube. The collection syringe can be attached to an optional stopcock 11 as a valve or turning plug which controls the flow of fluid from the PPP collection syringe to the blood collection tube. The collection syringe can be also attached to an optional filter unit (with or without a stopcock unit). The PRP collection syringe may be either pre-washed or un-washed, with activator such as Thrombin, $CaCl_2$, collagen solution, ADP or silicate solution or suspension. The PRP collection syringe may comprise two or more split barrels, when one of the barrels may contain activators or/and additives and another barrel can collect PRP. Alternatively, PRP may be transferred by the PRP collection syringe to another vessel containing activators and/or additives.

The remaining amount of the fraction comprising; PRP 7 which can be combined with WBCs, is drawn 170 using a PRP portion collection syringe 11, attached to the hub of the long sharp needle 11a or via attaching a syringe to another port of the stopcock 11c with an optional filter unit 11b.

In another embodiment of the invention, an optional stopcock 11 as a valve or turning plug controls the flow of fluid from the PPP collection syringe to the blood collection tube. In another embodiment of the invention a two or three-way stopcock can be used also to turn off the flow of one solution and turn on the flow of another. The PRP portion collection syringe 11 are transferred.

In another embodiment of the invention, using the method as described above, the platelets rich plasma (PRP) collection syringe may contain an additive selected from the group consisting of: Hyaluronic acid (HA), collagen, bone substitutes, allograft or autograft bone, previously derived autologous adult stem cells, $CaCl_2$, thrombin of human recombinant or animal origin, collagen, and any combination thereof. Furthermore, the PRP fraction that was collected may be transferred by a PRP collection syringe to another vessel which contains the aforementioned additives. The PRP collection syringe may comprise two or more split barrels, when one of the barrels may contain activators or/and additives and another barrel serves for PRP collection.

Furthermore, the PRP or stem cell concentrate may be mixed with hemostat or biodegradable scaffolds for internal or external (wounds, dentistry, for example) use.

Figure 2:
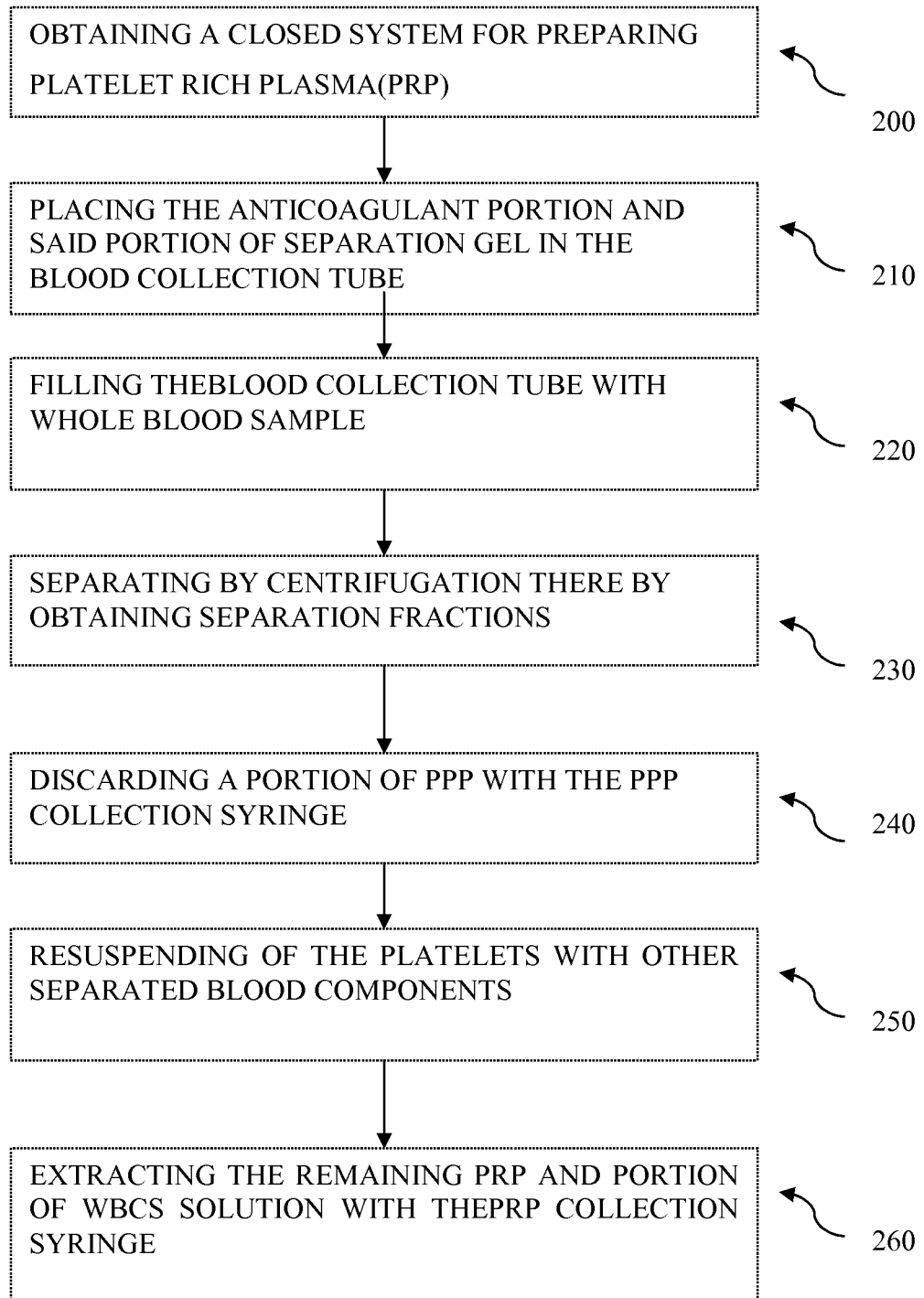
FIG. 2 illustrates a flow chart of a method for producing a WBC-selective PRP in a closed system, in accordance with a preferred embodiment of the present invention; and, FIG. 3 illustrates a flow chart of a method for producing an enriched cellular portion in a closed system, in accordance with a preferred embodiment of the present invention.

Reference is herein made to FIG. 2 which illustrates a procedure for preparing selective PRP. Whole blood sample can be drawn from a subject by using a conventional blood drawing device 200, having a vein needle, a flexible tube and separation tube adapter with a piercing member (holder attached to Luer adapter attached to PSV Butterfly). By piercing the central portion of the stopper and as a consequence of the vacuum inside the test tube, blood is withdrawn there into. Separation Gel and anti-coagulant, optionally included within the test tube, becomes mixed with the blood sample inhibiting clotting. Eventually, after disconnecting the tube from the blood drawing device, a test tube with a blood sample, optionally mixed with an anti-coagulant is obtained.

In other embodiments of the present invention, the blood can be drawn from a subject by using a conventional blood drawing device, such as PSV butterfly and syringe and transferred from the syringe into a non-vacuum tube.

In some exemplary embodiments of the invention, there is provided a method for producing of platelets rich plasma (PRP) in a closable system, the method comprising steps of:
(a) obtaining a closed system for preparing platelet rich plasma (PRP) 200 comprising: (i) a blood collection tube, (ii) an anticoagulant portion, (iii) a portion of separation gel, (iv) a platelets poor plasma (PPP) collection syringe including sharp long needle; and (v) a platelets rich plasma (PRP) collection syringe including sharp long needle and a filter unit;
(b) placing the anticoagulant portion and the portion of separation gel in the tube 210,
(c) filling the blood collection tube with whole blood sample 220, (d) separating by centrifugation thereby obtaining separation fractions comprising, a first fraction of RBCs with some granulocytes sediment, a second fraction of the gel, a third fraction of PRP, and fourth fraction of PPP solution 230, (e) discarding a portion of PPP with the PPP collection syringe comprising a sharp needle 240, (f) re-suspending of the platelets with other separated blood components 250, (g) extracting the remaining PRP and portion of WBCs solution with the PRP collection syringe 260 which may include a filter unit, such that a WBC-selective PRP is obtained.

In another embodiment of the invention the method as described above, comprises a filter unit of 3to about 50 µm.

In another embodiment of the invention the method as described above wherein the tube is selected from the group consisting of: a vacuum, a non-vacuum tube, a rigid tube, a non-rigid tube, a semi rigid tube, a plastic tube, a glass tube, and any combination thereof.

In another embodiment of the invention the method as described above wherein the separation gel is at density of 1.04 to about 1.09 g/cm$^3$.

In another embodiment of the invention the method as described above wherein the discarding up to 90% of PPP from the blood collection vacuum tube.

In another embodiment of the invention the method as described above wherein the discarding about 90% of PPP from the blood collection vacuum tube.

In another embodiment of the invention the method as described above, wherein the anticoagulant is selected from the group consisting of: buffer citrate, ACD, modified ACD (citric/citrate dextrose), heparinate salts, EDTA salts, iodo acetate salts, oxalate salts, fluoride salts as water solutions or lyophilized material or wet or dry spray on inner wall and so forth and any combination thereof.

In another embodiment of the invention the method as described above, wherein the anticoagulant comprises any type of anticoagulant designed for preventing clotting of blood.

In another embodiment of the invention the method as described above, wherein the platelets rich plasma (PRP) collection syringe may contain additives selected from the group consisting of: Hyaluronic acid (HA), collagen, bone substitutes, allograft or autograft bone, previously derived autologous adult stem cells, CaCl$_2$, thrombin of human recombinant or animal origin, collagen and any combination thereof. The PRP collection syringe may comprise at least two split-barrels, whilst one of the barrels may contain activators or/and additives and the another barrel is used for PRP collection. The PRP portion which was collected using the PRP collection syringe, may be transferred to another vessel which contains the aforementioned additives. Furthermore, the concentrated PRP or the stem cell fraction may be mixed with hemostat or biodegradable scaffolds for internal or external use (e.g. wounds, dentistry).

Figure 3:
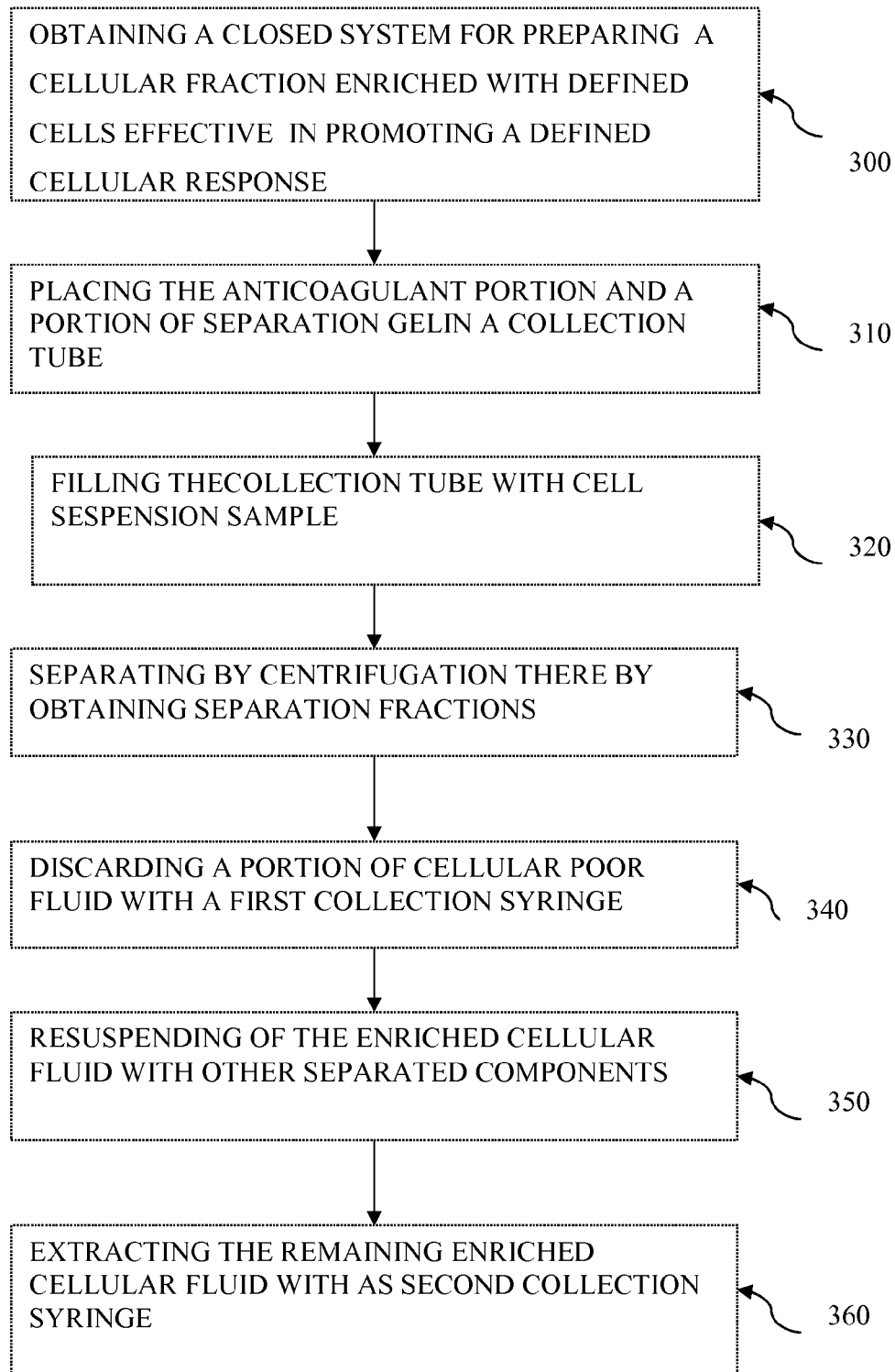

Reference is herein made to FIG. 3 which illustrates a method for producing of enriched stem cells sample, the method comprising steps of:
(a) obtaining a closable system for obtaining a cellular fraction enriched with defined cells effective in promoting a defined cellular response from an in vivo cellular sample, 300 comprising: (i) a collection tube for collecting a cell suspension (1); (ii) at least one stopper, (iii) an anticoagulant portion, (iv) a portion of separation gel, (v) a first collection syringe for collecting a cellular sample, (vi) a second collection syringe for collecting the enriched cellular portion and, (vii) at least one needle (10) for attaching to each the syringe.
(b) placing the anticoagulant portion and the portion of separation gel in the tube 310,
(c) filling cell suspension with cell culture sample 320, (d) separating by centrifugation there by obtaining separation fractions comprising, a first fraction of cell suspension, a second fraction of the gel, a third fraction of enriched cellular portion, and fourth fraction of poor cellular fluid 330, (e) discarding a portion of poor cellular fluid with the first collection syringe combined with the needle 340, (f) re-suspending of the cellular fluid with other separated cell components, (g) extracting the remaining enriched cellular portion with the enriched cellular portion collection syringe, optionally combined with a filter unit 350, such that an enriched selective stem cells fraction is obtained.

The system is adapted such that the cell poor portion is discardable with the first collection syringe with the needle. The second collection syringe with the needle are dimensionally configured for extraction of cells remaining after re-suspending of the enriched cellular portion. The term cell suspension is a peripheral blood sample or a stem cell sample containing cells such as bone marrow or adipose or umbilical cord blood stem cells.

In another embodiment of the present invention, a system for obtaining an enriched mesenchymal stem cell (MSC) or hematopoetic stem cells portion may be adapted, the system comprising:
(a) a collection tube for collecting cell suspension, (b) at least one stopper, (c) an anticoagulant portion, (d) a portion of separation gel, (e) a first collection syringe for collecting poor cellular fluid, (f) a second collection syringe for collecting enriched mesenchymal stem cell (MSC) portion (11) and (g) at least one needle (10) for attaching to each syringe. The system is closable to the atmosphere. The collection tube comprising the gel and the anticoagulant. The collection tube containing cell suspension is adapted such that, when containing the cell suspension and centrifuged after treatment yields separation fractions, a first fraction comprises red blood cells (RBCs), a second fraction comprises gel layer, a third fraction comprises cellular layer containing MSC or hematopoietic stem cells on top of the gel layer and a fourth fraction comprises poor cellular fluid.

The system is adapted such that the poor cellular fluid is discardable with the first collection syringe.

The second collection syringe with the needle are dimensionally configured for extraction of the enriched MSC portion remaining after re-suspending of the MSC portion.

The invention further provides a system for obtaining an enriched bone marrow fraction may be adapted, the system comprising: (a) a collection tube for collecting bone marrow, (b) at least one stopper, (c) an anticoagulant portion, (d) a portion of separation gel, (e) a first collection syringe for collecting fluid poor in cells, (f) a second collection syringe for collecting a portion enriched in bone marrow cells, and (g) at least one needle for attaching to each syringe.

The system is closable to the atmosphere. The collection tube for collecting bone marrow contains the gel and the anticoagulant; the tube containing the bone marrow is adapted such that when centrifuged after treatment yields separation fractions, a first fraction comprises primarily red blood cells (RBCs) sediment, a second fraction comprises gel layer, a third fraction comprises cellular fraction of enriched bone marrow cells on top of the gel layer and a fourth fraction comprises poor cellular fluid.

The poor cellular fluid is discarded using the first collection syringe.

The second collection syringe with the needle are dimensionally configured for extraction of the enriched bone marrow cells after re-suspending of the remaining bone marrow cells portion.

The system further comprises means for treating cell aspirate before the latter is applied into the collection tube.

The invention further provides a system for obtaining a low medium density fraction enriched with defined cells effective in promoting a defined cellular response from an in vivo cellular sample comprising: (a) a collection tube for collecting a cell suspension, (b) an anticoagulant portion to prevent clotting of cells, (c) a portion of separation gel, (d) a first collection syringe for collecting a cell depleted fluid;
(e) a second collection syringe for collecting the enriched cellular portion; and,
(d) at least one needle for attaching to each syringe.

The system is closable to the atmosphere. The cell suspension collection tube contains the gel and the anticoagulant. The tube is adapted such that, when containing cell suspension and centrifuged after treatment yields fractions of different densities, a first high density fraction, a second medium-high density fraction (3), a third medium-low density fraction on top of the gel layer and a fourth fraction low density fraction, the third medium-low density fraction substantially containing enriched defined cells; the enriched defined cells selected from the group consisting of enriched bone marrow stem cells, enriched MSC or platelet rich plasma (PRP).

In the foregoing description, embodiments of the invention, including preferred embodiments, have been presented for the purpose of illustration and description.

They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A system closable to the atmosphere for obtaining a portion enriched in mesenchymal (MSC) and/or hematopoetic stem cell (HSC), comprising:
   a. a collection tube for collecting cell suspension comprising at least one stopper for maintaining said collection tube closable to the atmosphere; an anticoagulant portion; and a portion of separation gel said gel having a density of about 1.04 $g/cm^3$ to about 1.09 $g/cm^3$, adapted for separating and acting as a barrier between fractions of said cell suspension formed after centrifugation;
   b. a first collection syringe for collecting poor cellular fluid portion poor in MSC and/or HSC;
   c. a second collection syringe for collecting said portion enriched in MSC and/or HSC, wherein said first collection syringe and said second collection syringe are adapted for simultaneous connection to the collection tube via a common connector to enable selective collection of said poor cellular fluid portion and said enriched portion; and
   d. at least one needle for attaching to each said syringe;
   wherein said second collection syringe comprises a filter unit having effective pore size of about 3-50 µm for obtaining MSC and/or HSC; further wherein, said collection tube containing said cell suspension and said gel are adapted such that, when containing the cell suspension and centrifuged after treatment yields separation fractions, a first fraction comprises primarily red blood cells (RBCs), a second fraction comprises said gel layer, a third fraction comprises cellular fraction containing enriched MSC and/or HSC on top of said gel layer and a fourth fraction comprises poor cellular fluid portion of platelet-poor plasma (PPP).

2. The system according to claim 1, wherein
   a. said first collection syringe is adapted to extract said poor cellular fluid portion;
   b. said second collection syringe with said needle are dimensionally configured for extraction of the enriched MSC and/or HSC portion remaining after re-suspending of said MSC portion; and/or
   c. said collection tube is a vacuum tube, a non-vacuum tube, a plastic tube, a glass tube, a rigid tube, a flexible tube, or a semi rigid tube.

3. A system closable to the atmosphere for obtaining an enriched bone marrow aspirate concentrate fraction comprising:
   a. a collection tube for collecting bone marrow comprising: at least one stopper for maintaining said collection tube closable to the atmosphere, an anticoagulant portion; and a portion of separation gel having a density of about 1.04 $g/cm^3$ to about 1.09 $g/cm^3$ adapted for separating and acting as a barrier between fractions of said bone marrow formed after centrifugation;
   b. a first collection syringe for collecting a poor cellular fluid portion from the collection tube;
   c. a second collection syringe for collecting enriched bone marrow cells, wherein said first collection syringe and said second collection syringe are adapted for simultaneous connection to the collection tube via a common connector to enable selective collection of said poor cellular fluid portion and said enriched portion; and, d. at least one needle for attaching to each said syringe;

wherein said second collection syringe comprises a filter unit having effective pore size of about 3-50 μm for obtaining enriched bone marrow aspirate concentrate;

further wherein said tube containing the bone marrow is adapted such that when centrifuged after treatment yields separation fractions in a sterile environment, a first fraction comprises primarily red blood cells (RBCs) sediment, a second fraction comprises a gel layer, a third fraction comprises enriched bone marrow nucleated cells on top of the gel layer and a fourth fraction comprises the poor cellular fluid portion of PPP.

4. The system according to claim 3, wherein
a. said poor cellular fluid portion is extracted using said first collection syringe;
b. said second collection syringe with said needle are dimensionally configured for extraction of the enriched bone marrow nucleated cells after re-suspending of the remaining bone marrow aspirate concentrate portion; and/or
c. said collection tube is a vacuum tube, a non-vacuum tube, a plastic tube, a glass tube, a rigid tube, a flexible tube, or a semi rigid tube.

5. A system for obtaining platelet rich plasma (PRP) comprising:
a. a collection tube for collecting whole blood comprising at least one stopper for maintaining said collection tube closed to atmosphere; a citrate-based anticoagulant; and a separation gel comprising polyolefin and having a density of about 1.04 to about 1.09 g/cm³;
b. a first collection syringe adapted to be connected to said collection tube for collecting platelet poor plasma (PPP) from the collection tube while said collection tube is closed to the atmosphere;
c. a second collection syringe adapted to be connected to said collection tube for collecting platelets rich plasma (PRP) from the collection tube while said collection tube remains closed to the atmosphere; and,
d. at least one needle for attaching to each said syringe;

wherein said separation gel forms a barrier between fractions of said blood after centrifugation: a first fraction comprises red blood cells (RBCs) sediment and granulocytes, a second fraction comprises gel layer, a third fraction comprises platelets and white blood cells on top of the gel layer, and a fourth fraction comprises platelet poor plasma (PPP).

6. The system according to claim 5, wherein
a. said collection tube is a vacuum tube, a non-vacuum tube, a plastic tube, a glass tube, a rigid tube, a flexible tube, or a semi rigid tube; and
b. said first collection syringe is configured for collecting and discarding at least 50% and up to 90% of said platelet poor plasma (PPP) in said collection tube.

7. The system according to claim 5, wherein
said second collection syringe for collecting platelets rich plasma (PRP) contains an additive selected from the group consisting of: Hyaluronic acid (HA), collagen, allograft bone, auto graft bone, bone substitute, autologous adult stem cells, $CaCl_2$, thrombin, collagen, hemostat scaffold or a combination thereof.

8. A system closable to the atmosphere for obtaining platelet rich plasma (PRP) comprising:

a. a vacuum collection tube for collecting blood comprising: at least one stopper for maintaining said collection tube closable to the atmosphere; a citrate-based anticoagulant; and a separation gel having a density of about 1.04 g/cm³ to about 1.09 g/cm³ adapted for separating and acting as a barrier between fractions of said cell suspension formed after centrifugation;
b. a first collection syringe for collecting platelet poor plasma (PPP);
c. a second collection syringe for collecting platelet rich plasma (PRP) portion, wherein said first collection syringe and said second collection syringe are adapted for simultaneous connection to the collection tube via a common connector to enable selective collection of said poor cellular fluid portion and said enriched portion; and
d. at least one needle for attaching to each said syringe;

wherein said second collection syringe for collecting enriched platelet rich plasma (PRP) portion further comprises a filter unit having effective pore size of about 3-50 μm for obtaining WBC-selective PRP.

9. The system according to claim 8, wherein
a. said collection tube is a vacuum tube, a non-vacuum tube, a plastic tube, a glass tube, a rigid tube, a flexible tube, or a semi rigid tube.

10. The system according to claim 8, further comprising at least one of the following:
a. a stopcock adapted as a turning plug which controls the flow of fluid from said blood collection tube to said first collection syringe;
b. a stopcock adapted as a turning plug which allows one way flow of fluid from said blood collection tube to said second collection syringe; and
c. said anticoagulant is selected from the group consisting of: buffer citrate, acid citrate dextrose (ACD), modified ACD (citric/citrate dextrose), heparinate salt, EDTA salt, iodo acetate salt, oxalate salt, fluoride salt and any combination thereof.

11. The system according to claim 8, wherein:
a. said first collection syringe for collecting platelet poor plasma (PPP) is adapted for discarding PPP.

12. The system according to claim 8, wherein said second collection syringe for collecting platelet rich plasma (PRP) contains an additive selected from the group consisting of: Hyaluronic acid (HA), collagen, allograft bone, autograft bone, bone substitute, autologous adult stem cells, CaCl2, thrombin, collagen and any combination thereof.

13. A method for producing platelet rich plasma (PRP), comprising:
providing a collection tube for collecting blood, the tube comprising at least one stopper for maintaining said collection tube closed to atmosphere; a citrate based anticoagulant; and a separation gel comprising polyolefin and having a density of 1.04 g/cm³ to about 1.09 g/cm³, adapted to act as a barrier and as a separating element between fractions of said blood after centrifugation;
extracting a whole blood sample from a patient into said collection tube;
separating the whole blood sample by centrifugation to obtain separation fractions comprising a first fraction of red blood cell sediment and granulocytes, a second fraction of said gel, a third fraction containing platelets and white blood cells (WBCs) on top of said gel, and a fourth fraction of platelet poor plasma (PPP);

extracting 50-90% of said PPP from said collection tube with a first collection syringe while the collection tube remains closed to the atmosphere;

re-suspending the platelets in the collection tube; and extracting PRP from said collection tube including a portion of WBCs remaining in said collection tube on top of the gel with a second collection syringe while the collection tube remains closed to the atmosphere.

14. The method according to claim 13, further comprising including allograft bone or autograft bone in said second syringe and extracting said PRP into said second syringe with said allograft bone or autograft bone.

15. The method according to claim 13, comprising extracting about 90% of said PPP with the first collection syringe.

16. The method according to claim 13, wherein PRP including a portion of WBCs in said extracting step is WBC-selective PRP having a WBC concentration less than 50% of that in said whole blood.

* * * * *